(12) United States Patent
Parker

(10) Patent No.: US 6,515,168 B1
(45) Date of Patent: Feb. 4, 2003

(54) PROCESS FOR PREPARING N-PHOSPHONOMETHYL IMINODIACETIC ACID

(75) Inventor: Brian Parker, County Dublin (IE)

(73) Assignees: Crop Protection Holdings SDN BHD, Selanger (MY); Agriguard Limited, Dublin (IE)

( * ) Notice: Subject to any disclaimer, the term of this patent is extended or adjusted under 35 U.S.C. 154(b) by 0 days.

(21) Appl. No.: 09/743,380

(22) PCT Filed: Jul. 8, 1999

(86) PCT No.: PCT/IE99/00062

§ 371 (c)(1),
(2), (4) Date: Mar. 19, 2001

(87) PCT Pub. No.: WO00/02888

PCT Pub. Date: Jan. 20, 2000

(30) Foreign Application Priority Data

Jul. 9, 1998 (IE) .............................. S980552

(51) Int. Cl.$^7$ ............................. C07F 9/22; C07F 9/28; A01N 57/18
(52) U.S. Cl. ............................. 562/17; 504/206
(58) Field of Search ............................. 562/17; 504/206

(56) References Cited

U.S. PATENT DOCUMENTS

| | | | |
|---|---|---|---|
| 2,895,989 A | 7/1959 | Sexton | |
| 3,808,269 A | 4/1974 | Bragdon et al. | |
| 3,904,668 A | 9/1975 | Guadette et al. | 260/465.5 |
| 3,950,402 A * | 4/1976 | Franz | 260/502.5 |
| 3,954,848 A | 5/1976 | Franz | |
| 3,969,398 A | 7/1976 | Hershman | |
| 4,002,672 A | 1/1977 | Smith | |
| 4,147,719 A | 4/1979 | Franz | |
| 4,579,689 A | 4/1986 | Hershman et al. | |
| 4,582,650 A | 4/1986 | Felthouse | |
| 4,696,772 A | 9/1987 | Chou | |
| 4,724,103 A * | 2/1988 | Gentilcore | 260/502.5 |
| 4,775,498 A | 10/1988 | Gentilcore | 260/502.5 |
| 4,782,183 A | 11/1988 | Goto | 562/526 |
| 4,931,585 A | 6/1990 | Pelyva et al. | |
| 5,095,140 A | 3/1992 | Fields, Jr. | |
| 5,179,228 A | 1/1993 | Ramon et al. | |
| 5,312,973 A | 5/1994 | Donadello | |
| 5,527,953 A | 6/1996 | Jones et al. | |
| 5,620,584 A | 4/1997 | Reetz et al. | 205/334 |
| 5,688,994 A | 11/1997 | Baysdon et al. | |
| 5,689,000 A | 11/1997 | Ebner et al. | 562/539 |
| 6,118,022 A | 9/2000 | Cullen | |

FOREIGN PATENT DOCUMENTS

| | | |
|---|---|---|
| EP | 155926 B1 | 8/1988 |
| GB | 2215720 A | 9/1985 |
| WO | WO 94/24091 | 10/1994 |

* cited by examiner

Primary Examiner—Mukund J. Shah
Assistant Examiner—Zachary C. Tucker
(74) Attorney, Agent, or Firm—Christie, Parker & Hale, LLP

(57) ABSTRACT

The present invention relates to an energy and effluent saving process for the production of N-phosphonomethyl iminodiacetic acid (PMIDA), an intermediate in the preparation of glyphosate. An alkali metal salt of iminodiacetic acid is reacted with phosphorous acid and a strong mineral acid, or a source thereof to form iminodiacetic phosphite and the alkali metal salt of the strong mineral acid. After removal of the latter salt, the iminodiacetic phosphite is converted to PMIDA by reaction with formaldehyde. PMIDA is recovered and the solution remaining can be recycled in the process.

11 Claims, No Drawings

PROCESS FOR PREPARING N-PHOSPHONOMETHYL IMINODIACETIC ACID

This application is a national stage filing under 35 U.S.C. 371 of International Application number PCT/IE99/00062, filed Jul. 8, 1999, and published by the International Bureau, in English, Jan. 20, 2000.

This invention relates to an improved process for preparing N-phosphonomethyl iminodiacetic acid (PMIDA) also known as N,N-diacetic acid aminomethylene-phosphonic acid. PMIDA is an intermediate in the preparation of N-phosphonomethyl glycine (PMG) also known as glyphosate, which is a well-known translocated, postemergence, broad-spectrum herbicide.

A process which is currently widely used for preparing PMIDA involves reacting an alkali metal salt of iminodiacetic acid (IDA) in aqueous strong mineral acid solution with phosphorous acid and formaldehyde. Such a process is described in U.S. Pat. Nos. 4,724,103 and 4,775,498. In this process the strong mineral acid salt of IDA and the alkali metal salt of the strong mineral acid are formed initially. The strong mineral acid salt of IDA has a low solubility, so that the alkali metal salt of the mineral acid cannot be removed easily at this stage and therefore remains in the reaction medium. Subsequent phosphonomethylation of the IDA mineral acid salt results in a mixture of PMIDA and the alkali metal salt. The latter salt is separated from the PMIDA by the addition of water to the mixture in a quantity sufficient to dissolve the alkali metal salt. The PMIDA is then recovered from the solution by precipitation and filtration. The main disadvantage of this process is that large quantities of effluent are generated because of the necessity to add water to dissolve the alkali metal salt, which complicates the feasibility of recycling this liquor which contains valuable raw materials.

It is therefore an object of the present invention to provide a process for preparing PMIDA which avoids or minimises the disadvantages of the prior art.

According to the present invention there is provided a process for preparing N-phosphonomethyl iminodiacetic acid (PMIDA), which process comprises the following steps:

(a) reacting an alkali metal salt of iminodiacetic acid (IDA) with phosphorous acid and a strong mineral acid or a source of these acids to form iminodiacetic phosphite and an alkali metal salt of the strong mineral acid;

(b) removing at least a part of he alkali metal salt formed in step (a);

(c) reacting the iminodiacetic phosphite formed in step (a) with phosphorous acid and a strong mineral acid or a source of these acids, together with formaldehyde, to form PMIDA in reaction medium; and, if desired, (d) isolating the PMIDA; and (e) optionally recycling the medium remaining following the isolation of the PMIDA in the process.

The alkali metal salt of IDA is preferably the disodium or dipotassium salt.

Strong mineral acids which may be used in the process of the invention include hydrochloric, hydrobromic, hydriodic and sulphuric acids. Hydrochloric acid is preferred.

A particularly preferred source of phosphorous acid is $PCl_3$ which can also provide hydrochloric acid when hydrolysed in aqueous medium.

The intermediate compound, iminodiacetic phosphite (IDA.$H_3PO_3$), is novel and forms a further aspect of this invention.

In step (a) of the process of the invention, the amount of strong mineral acid added or generated should be just sufficient to neutralise the IDA alkali metal salt and any free alkali (such as NaOH) present, preferably about 0.5 to 1.5, more preferably about 0.5 to 1.0, equivalents of acid. Excessive amounts of the strong mineral acid must be avoided as any excess will lead to the formation of the mineral acid salt of IDA which is not desired in the present process. In the present process, the reaction of the IDA salt with phosphorous acid and a strong mineral acid or a source of these acids, such as $PCl_3$, leads to the formation of the novel intermediate, iminodiacetic phosphite, and the alkali metal salt of the strong mineral acid. After cooling to about 85° C., the alkali metal salt is removed, conveniently by filtration, in an amount sufficient to avoid coprecipitation of the salt with the final product (PMIDA). Because iminodiacetic phosphite is highly soluble in the reaction medium and the alkali metal salt is not, the alkali metal salt can be readily removed at this stage (step (b)).

The reaction in step (a) is carried out at a temperature in the range of from 40° C. to 75° C., preferably about 45° C. to 65° C. for about 1–4 hours. The reaction mixture is cooled to a temperature between 80° C. and 90° C. before removal of the alkali metal salt of the mineral acid. The iminodiacetic phosphite solution at this stage is maintained at a temperature greater than 60° C., preferably between 70° C. and 100° C.

In step (c), the iminodiacetic phosphite is reacted with a further amount of phosphorous acid and a strong mineral acid or a source of these acids, and formaldehyde at a temperature in the range of from 105° C. to 135° C. for a period of about 30 minutes to 4 hours. After cooling to about 30° C., PMIDA is formed as a solid precipitate in the reaction medium. Subsequent separation of PMIDA (step (d)) can be achieved by conventional methods such as filtration or centrifugation.

The reaction medium from step (d) is preferably recycled in the process of the invention. In the recycling process, alkali such as NaOH is added to the iminodiacetic phosphite if necessary to at least partially neutralize free acid such as HCl. Phosphorous acid and a strong mineral acid, or a source of these acids such as $PCl_3$, are added to the recycle medium. Following reaction at a temperature between 45° C. and 65° C. for a period of about 30 minutes to 4 hours, the reaction product is cooled to about 20° C.–40° C. and a sufficient amount of the alkali metal salt of the strong mineral acid is removed as a wet cake, conveniently by filtration, to allow recycling. The salt is easily removed at this stage because the presence of free acid is high. Where the salt is NaCl and the acid is HCl, it is well known that the solubility of NaCl in water in the presence of 28–30% HCl is essentially zero. A portion of the resultant filtrate containing $H_3PO_3$ and strong mineral acid is then reacted with the alkali metal salt of IDA to form iminodiacetic phosphite and the alkali metal salt of the strong mineral acid, as described hereinabove for step (a). The amount of strong mineral acid present should not be excessive but should be sufficient to neutralize any free alkali and IDA salt, so that iminodiacetic phosphite and not the strong mineral acid salt of IDA is formed. The alkali metal salt is then removed as described above.

The resulting iminodiacetic phosphite solution is kept hot, typically at a temperature greater than 60° C. and preferably between 70° C. and 100° C. Water can be boiled off at this stage if necessary to ensure proper water balance and maximum liquor recycle The remainder of the filtrate generated above is then added to the iminodiacetic phosphite solution, together with formaldehyde and reacted as described above for step (c) to form PMIDA and further reaction medium which can be recycled in the process.

Iminodiacetic acid (IDA) or a salt thereof can be prepared as described in U.S. Pat. Nos. 5,689,000; 5,620,584; or 4,782,183; or 3,904,668 or WO-A-94/24091. IDA can also be obtained commercially and the desired salt prepared in known manner.

The yield of PMIDA prepared according to the process of the invention can be as high as 91%. Furthermore, because the alkali metal salt of the mineral acid formed during the reaction can be removed as a wet cake, the mother liquor containing valuable raw materials can be recycled thereby greatly reducing the amount of effluent generated and increasing the efficiency of the process in an environmentally friendly manner. The mother liquor can contain approximately 5% free HCl based on a 60% liquor recycle. Higher recycle rates, such as 80%, can also be achieved as can be seen in the Examples hereinafter.

Unless otherwise stated, the disodium iminodiacetate (DSIDA) used in the Examples was prepared by neutralizing iminodiacetic acid (supplied by Aldrich) with 2.2 mole equivalents of 50% NaOH.

EXAMPLE 1

For the purpose of simulating real mother liquor recycle conditions, a batch of synthetic liquor was generated. 37% HCl solution from Aldrich was analysed and found to contain 36.2% HCl. 306.8 g of water, 82.6 g of NaCl and 59.3 g of the above HCl solution were added to a 1000-ml conical flask. The resultant mixture was stirred for 20 minutes at 35° C. and will be referred to as 'synthetic liquor' hereinafter.

The synthetic liquor was added to a 1-litre reactor equipped with a heating mantle, condenser, overhead stirrer and thermometer. The contents were heated and held between 45° C. and 65° C. and 152.0 g of $PCl_3$ were pumped in over a period of 122 minutes. Addition rates of the $PCl_3$ were varied in an attempt to control the temperature. The reactor contents were cooled to about 40° C. and filtered using a 1-litre Buchner filtering apparatus having a funnel with a diameter of approximately 10 cm using Whatman filter paper. The filter cake was retained on the filtering apparatus.

The filtrate was split into two portions of 365.0 g (portion A) and 141.0 g (portion B). 432 g of 41% DSIDA (disodium iminodiacetate) were added to the reactor at about 65° C. 56.0 g of 50% NaOH were also added. Portion A was added and 150 g of $H_2O$ were removed at the boil. The contents were filtered at about 70° C. on the apparatus used for the previous filtration as described above. The filter cake was washed with 30 ml of iced water from a spray bottle and the combined cake was dried in an oven. The solid was dried and 114.0 g of a solid later analysed as 98.7% NaCl was recovered.

The filtrate obtained immediately above was weighed at 695.0 g. 521.1 g of this were added back into the reactor. The remainder of the liquor, portion B, was added to the reactor also. The contents were heated to the boil and 88.70 g of 44% formaldehyde were pumped into the reactor over a period of two hours. Simultaneously, the remainder of the filtrate (173.9 g) was pumped in over 110 minutes. The contents of the reactor were held for another 60 minutes at the boil before being cooled to about 35° C. The contents were then filtered and the filter cake was washed with 50 g of iced $H_2O$ from a spray bottle. The filter cake was dried overnight in an oven and subsequently analysed by HPLC.

197.0 g of 99.2% PMIDA were recovered corresponding to an 86.1% yield of theoretical.

749.0 g of liquor were recovered which was subsequently analysed and found to contain approximately 4.80% HCl and 18.1% NaCl.

EXAMPLE 2

60% of the mother liquor generated or 449.0 g from Example 1 were retained for recycle This liquor was charged to a 1-litre reactor. 152.1 g of $PCl_3$ were pumped into the reactor as described in Example 1. The temperature was held again between 45° C. and 65° C. The addition time was regulated over 110 minutes. The reactor contents were cooled to about 40° C. and filtered as described in Example 1. The filter cake was retained on the filtering apparatus for the next filtration step.

The filtrate was again split into two portions of 365.1 g (portion A) and 142.1 g (portion B). 432.0 g of 41% DSIDA were charged to the reactor at about 65° C. and 56.0 g of 50% NaOH were also added. Portion A liquor was subsequently added. The contents were heated to the boil and 150 g of water were distilled off. The contents were filtered through the same apparatus used in the first filtration described above at about 70° C. The filter cake was then washed with about 30 g of iced $H_2O$. The cake was dried and 115.0 g of a solid later analysed as 98.1% NaCl was recovered.

The hot filtrate and wash were split into two portions of 522.0 g and 173.5 g. 522.0 g were added back into the reactor, together with the remaining liquor, portion B. The contents were heated to the boil and 88.7 g of 44% $CH_2O$ were metered into the reactor over a period of 114 minutes. Simultaneously 173.5 g of the filtrate were pumped in over 108 minutes. The contents were held at the boil for another hour approximately. The reactor and contents were then cooled to about 40° C. and filtered as described in Example 1. The filter cake was thoroughly washed with 50 g of iced $H_2O$. 747.20 g of the filtrate were retained for recycle and the cake was dried in an oven overnight.

The filter cake was analysed by HPLC and found to contain 99.1% PMIDA. 201.8 g of dry cake were recovered corresponding to a 88.1% yield of theoretical. Liquor analysis showed 4.8% HCl and 18.0% NaCl.

EXAMPLE 3

448.3 g of the liquor retained from Example 2 were charged to the reactor. 151.8 g of $PCl_3$ were pumped in over 118 minutes as described in Example 1. The temperature was controlled between 45° C. and 65° C. during the addition. The contents were cooled to 40° C. and filtered as in Example 1 and the cake was retained on the filtering apparatus. The filtrate was split into two parts, portion A containing 364.0 g and portion B containing 141.0 g.

432.0 g of 41% DSIDA were charged to the reactor as described in Example 1. 56.0 g of 50% NaOH were also added and portion A liquor was subsequently added. The contents were heated to the boil and 150 g of water were distilled off. The contents were filtered through the apparatus retained from the filtration carried out immediately above at about 70° C. The filter cake was then washed with about 30 g of iced $H_2O$. The cake was dried and 115.5 g of a solid later analysed as 98.8% NaCl was recovered.

The hot filtrate and wash were split into two portions of 520.1 g and 173.4 g. 520.1 g were added back into the reactor, together with portion B. The contents were heated to the boil and 88.7 g of 44% $CH_2O$ were pumped into the reactor over a period of 118 minutes. 173.4 g of the filtrate were simultaneously pumped in over 111 minutes. The contents of the reactor were held for a further hour at the boil prior to being cooled to about 40° C. The contents were filtered. The filter cake was washed with 50 g of iced water. The cake was dried overnight in an oven and analysed by HPLC. The dry cake, 206.1 g, was found to contain 99.4% PMIDA. This corresponds to a 90.2% yield of theoretical.

The liquor was weighed at 738.1 g and retained for recycle. Liquor analysis showed 4.9% HCl and 185% NaCl.

EXAMPLE 4

443.0 g of the liquor retained from Example 3 were charged to the reactor. 152.0 g of $PCl_3$ were pumped in over 118 minutes as described in Example 1. The temperature was controlled between 45° C. and 65° C. during the addition. The contents were cooled to 40° C. and filtered and the cake was retained on the filtering apparatus as in Examples 1–3. The filtrate was split into two parts, portion A containing 360.1 g and portion B containing 141.0 g.

432.0 g of 41% DSIDA were charged to the reactor as described in Example 1 and 56.0 g of 50% NaOH were also added. Portion A liquor was subsequently added. The contents were heated to the boil and 150 g of water were distilled off. The contents were filtered through the apparatus retained from the above filtration at about 70° C. The filter cake was then washed with about 30 g of iced $H_2O$. The cake was dried and 114.0 g of a solid later analysed as 98.9% NaCl was recovered.

The hot filtrate and wash were split into two portions of 518.1 g and 172.5 g. 518.1 g were added back into the reactor, together with portion B. The contents were heated to the boil and 88.7 g of 44% $CH_2O$ were pumped into the reactor over a period 120 minutes. Simultaneously 172.5 g of the filtrate were pumped in over 110 minutes. The contents of the reactor were held for a further hour at the boil prior to being cooled to about 40° C. The contents were filtered and the filter cake was washed with 50 ml of iced water. The cake was dried overnight in an oven and analysed by HPLC. The dry cake, 208.1 g, was found to contain 99.4% PMIDA. This corresponds to a 91.1% yield of theoretical.

The liquor was weighed at 730.2 g and retained for recycle. Liquor analysis showed 4.7% HCl and 18.6% NaCl.

EXAMPLE 5

448.5 g of the liquor retained from Example 4 were charged to the reactor. 151.9 g of $PCl_3$ were pumped in over 118 minutes as described in Example 1. The temperature was controlled between 45° C. and 65° C. during the addition. The contents were cooled to 40° C. and filtered as in Example 1 and the cake was retained on the filtering apparatus. The filtrate was split into two parts, portion A containing 356.3 g and portion B containing 139.5 g.

432.0 g of 41% DSIDA were charged to the reactor as described in Example 1 and 56.0 g of 50% NaOH were also added. Portion A liquor was subsequently added. The contents were heated to the boil and 150 g of water were distilled off. The contents were filtered through the apparatus retained from the first filtration above at about 70° C. The filter cake was then washed with about 30 g of iced $H_2O$. The cake was dried and 117.1 g of a solid later analysed as 98.6% NaCl were recovered.

The hot filtrate and wash were split into two portions of 516.0 g and 172.1 g. 516.0 g were added back into the reactor, together with portion B. The contents were heated to the boil and 88.7 g of 44% $CH_2O$ were pumped into the reactor over a period 115 minutes. Simultaneously 172.1 g of the filtrate were pumped in over approximately 108 minutes. The contents of the reactor were held for a further hour at the boil prior to being cooled to about 40° C. The contents were filtered. The filter cake was washed with 50 g of iced water. The cake was dried overnight in an oven and analysed by HPLC. The dry cake, 209.7 g, was found to contain 98.7% PMIDA. This corresponds to a 91.2% yield of theoretical.

The liquor was weighed at 723.8 g and retained for recycle. Liquor analysis showed 4.9% HCl and 18.6% NaCl.

EXAMPLE 6

1. A 500-ml Erlenmeyer flask with a magnetic stir bar was placed in an ice bath and charged with 164.2 g (charge 1) of recycle liquor. For the purpose of simulating real liquor recycle conditions, a batch of synthetic liquor was generated by mixing the following components in a 2-litre Erlenmeyer flask. The mixture was heated to 40° C. and stirred on a magnetic stir plate for 2 hours.

528 g $H_2O$ 207.7 g of 36.1% HCl 118 g of NaCl 25 g PMIDA (essentially 100%)

15 g of hydoxymethyl phosphonic acid (essentially 100%)

30 g of N-methyl IDA (essentially 100%)

42 g of 70% phosphorous acid 34 g of 44% formaldehyde

2. $PCl_3$ (101.0 g) (charge 2) was pumped below the surface of the liquor at about 0.5 g/minute with rapid stirring.

3. After about half the $PCl_3$ had been added, the $PCl_3$ pump was stopped and 41% DSIDA (432 g)(charge 3) was charged.

4. When the temperature of the flask had cooled back down to about 35° C. the flow of $PCl_3$ was restarted.

5. When all the $PCl_3$ had been added, 50% NaOH (35.0 g)(charge 4) was charged.

6. The flask was weighed, then transferred to a hot plate and 365.7 g of water were evaporated by boiling.

7. The hot slurry was vacuum filtered to isolate the NaCl formed. The NaCl was washed with two 25 ml portions of water.

8. A 1-litre glass pressure reactor (with threaded Teflon top drilled and tapped to receive two ⅛ inch Swagelok to ⅛ inch FNPT (female national pipe thread) and 1 throughbored ¼ inch Swagelok to ⅛ inch FNPT fittings) containing a magnetic stir bar, was charged with 412.0 g recycle liquor (charge 5) and placed in an ice bath.

9. $PCl_3$ (43.5 g)(charge 6) was pumped into the rapidly stirred liquor at approx. 0.5 g/min.

10. The combined IDA solution and NaCl wash water were then charged to the 1-litre reactor and the reactor was sealed.

11. A ¼ inch teflon coated RTD (resistance thermal detector) was inserted through the ¼ inch Swagelok fitting and the stirred contents were heated to 105° C. at which time the reactor vent valve in one of the ⅛ inch Swagelok fittings was closed (the same fitting was also piped to a pressure relief valve set at 60 psi).

12. Heating continued until the temperature reached 125° C. The 44% formaldehyde (85.2 g)(charge 7) was then pumped in at approx 2 g/min through the third Swagelok fitting.

13. The temperature was maintained between 128 and 130° C. during the formaldehyde addition and for an additional 45 minutes after the addition of formaldehyde was complete.

14. The batch was cooled to 30° C. with a stream of compressed air and the slurry was transferred to a 2-litre Erlenmeyer flask containing 115 g of water.

15. The PMIDA slurry was vacuum filtered.

16. Liquor (576.2 g)(mother liquor) was set aside for analysis and the next run. The PMIDA cake was washed with 3×50 ml of water.

17. The PMIDA was dried overnight in an oven and weighed at 200.1% (Yield). Chelometric titration with copper showed the material to be 99.7% PMIDA, equivalent to an 87.9% recovery.

18. The combined purge liquor and wash were neutralized to pH 1.2 with 50% NaOH and stirred overnight. An additional 4.4 g of solid were recovered.

19. The final recycle liquor (from run 4) was analyzed by HPLC (high performance liquid chromatography) and found to contain:

| | |
|---|---|
| PMIDA | 2.8% |
| IDA | Not detected |
| Hydroxymethyl phosphonate | 1.7% |
| Methyl IDA | 3.2% |
| $H_3PO_3$ | 3.4% |
| HCHO | 1.5% |

The following charges were used for subsequent experiments. The procedure outlined above in this Example and the same equipment as described were used in all cases.

Summary of experiments for 70% liquor recycle

| Charge | Material | Run 1 (g) | Run 2 (g) | Run 3 (g) | Run 4 (g) |
|---|---|---|---|---|---|
| Part 1 | | | | | |
| 1 | Liquor | 164.2 | 165.0 | 163.4 | 164.1 |
| 2 | $PCl_3$ | 101.0 | 100.9 | 100.9 | 101.0 |
| 3 | $DSIDA_{2.2}$ | 432.1 | 432.1 | 432.0 | 432.1 |
| 4 | 50% NaOH | 35.0 | 35.4 | 35.2 | 35.3 |
| 5 | $H_2O$ out | 265.7 | 266.9 | 266.4 | 266.3 |
| Part 2 | | | | | |
| 5 | Liquor | 412.0 | 414.0 | 413.2 | 411.0 |
| 6 | $PCl_3$ | 43.5 | 42.0 | 43.6 | 43.5 |
| 7 | $CH_2O$ (44%) | 85.2 | 82.1 | 82.3 | 82.1 |
| Recovery | | | | | |
| | PMIDA | 200.1 | 204.5 | 202.1 | 208.2 |

It will be obvious to those familiar in the art that higher concentrations of reactants and larger mother liquor recycle rates can be employed without departing from the scope of this invention.

While the invention has been described in terms of various embodiments, it will be appreciated that various modifications, substitutions, omissions and changes may be made without departing from the scope thereof.

What is claimed is:

1. A process for preparing N-phosphonomethyl iminodiacetic acid (PMIDA), which process comprises the following steps:

(a) reacting an alkali metal salt of iminodiacetic acid (IDA) with phosphorous acid and a sufficient amount of strong mineral acid or source of these acids to preferentially form iminodiacetic phosphite and an alkali metal salt of the strong mineral acid rather than a mineral acid salt of IDA;

(b) removing at least part of the alkali metal salt formed in step (a); and (c) reacting the iminodiacetic phosphite formed in step (a) with phosphorous acid and a strong mineral acid or source of these acids, together with formaldehyde, to form PMIDA in reaction medium.

2. The process according to claim 1 additionally comprising isolating the PMIDA formed in step (c).

3. The process, according to claim 2 additionally comprising recycling in the process, the medium remaining following isolation of the PMIDA.

4. The process according to claim 1, wherein in step (a) an aqueous solution of the alkali metal salt of IDA is used.

5. The process according to claim 1, wherein the alkali metal salt of IDA is the disodium or dipotassium salt.

6. The process according to claim 1, wherein in step (a) the source of phosphorous acid and the strong mineral acid is $PCl_3$.

7. The process according to claim 1, wherein in step (c) the source of phosphorous acid and the strong mineral acid is $PCl_3$.

8. A process for the preparation of PMIDA, comprising providing iminodiacetic phosphite, and reacting it with phosphorous acid and a strong mineral acid or a source of these acids, together with formaldehyde, to form PMIDA.

9. The process according to claim 1, further comprising a step of converting the PMIDA formed in step (c) to N-phosphonomethyl glycine.

10. The process according to claim 1, wherein about 0.5 to 1.5 mole equivalents of the strong mineral acid or source of these acids is utilized to neutralize the alkali metal salt of IDA and any free alkali present.

11. The process according to claim 1, wherein about 0.5 to 1.0 mole equivalents of the strong mineral acid or source of these acids is utilized to neutralize the alkali metal salt of IDA and any free alkali present.

* * * * *